United States Patent [19]
De Santis

[11] Patent Number: 5,469,860
[45] Date of Patent: Nov. 28, 1995

[54] FINE NEEDLE ASPIRATION CYTOLOGY DEVICE SYRINGE HOLDER

[76] Inventor: Stephen A. De Santis, 23802 Inverness Pl., Laguna Niguel, Calif. 92677

[21] Appl. No.: 331,283

[22] Filed: Oct. 27, 1994

Related U.S. Application Data

[63] Continuation-in-part of Ser. No. 225,594, Apr. 11, 1994.

[51] Int. Cl.⁶ ..................................................... A61B 17/00
[52] U.S. Cl. ............................................ 128/765; 128/749
[58] Field of Search ..................... 128/749, 753, 128/765, 763; 604/223, 224, 227, 228, 198

[56] References Cited

U.S. PATENT DOCUMENTS

| | | | |
|---|---|---|---|
| Re. 34,056 | 9/1992 | Lindgren et al. | 128/754 |
| 2,892,457 | 6/1959 | Sturtz | 604/223 |
| 3,517,668 | 6/1970 | Brickson | 604/223 X |
| 3,561,429 | 2/1971 | Jewett et al. | 128/2 |
| 3,819,091 | 6/1974 | Hollender | 604/223 X |
| 3,844,272 | 10/1974 | Banko | 128/2 B |
| 3,905,365 | 9/1975 | Colombo | 604/223 X |
| 4,461,305 | 7/1984 | Cibley | 128/754 |
| 4,594,073 | 6/1986 | Stine | 128/765 X |
| 4,605,011 | 8/1986 | Naslund | 128/752 |
| 4,708,147 | 11/1987 | Haaga | 128/753 |
| 4,711,250 | 12/1987 | Gilbaugh, Jr. et al. | 128/765 |
| 4,776,346 | 10/1988 | Bersha et al. | 128/754 |
| 4,781,700 | 11/1988 | Vicario | 128/765 X |
| 4,893,635 | 1/1990 | de Groot et al. | 128/754 |
| 4,907,598 | 3/1990 | Bauer | 128/753 |
| 4,950,265 | 8/1990 | Taylor | 606/1 |
| 4,982,739 | 1/1991 | Hemstreet et al. | 128/750 |
| 5,115,816 | 5/1992 | Lee | 128/749 |
| 5,159,933 | 11/1992 | Hut | 128/753 |
| 5,183,052 | 2/1993 | Terwilliger | 128/753 |
| 5,213,110 | 5/1993 | Kedem et al. | 128/754 |
| 5,220,926 | 6/1993 | Jones | 128/754 |
| 5,224,470 | 7/1993 | Schnepp-Pesch et al. | 128/753 |
| 5,241,969 | 9/1993 | Carson et al. | 128/754 |
| 5,246,011 | 9/1993 | Caillouette | 128/753 |
| 5,249,582 | 10/1993 | Taylor | 128/754 |

Primary Examiner—Sam Rimell
Attorney, Agent, or Firm—Stetina Brunda & Buyan

[57] ABSTRACT

A fine needle aspiration cytology device for extracting tissue samples for cytologic evaluation is disclosed. The device comprises a handle and generally U-shaped slide member with trigger attachable thereto. The handle is designed and configured to releasably engage a conventional syringe. The slide is designed to slidably engage with the handle and is provided with a slot at the base thereof for retaining the plunger of the When interconnected, the slide may move in forward or rearward positions relative the handle and further, when interconnected with a syringe, may selectively control the axial position of the plunger relative the syringe. In a preferred embodiment, the device is further provided with a manually adjustable locking detent mechanism that may releasably maintain the handle and slide in rigid connection.

17 Claims, 9 Drawing Sheets

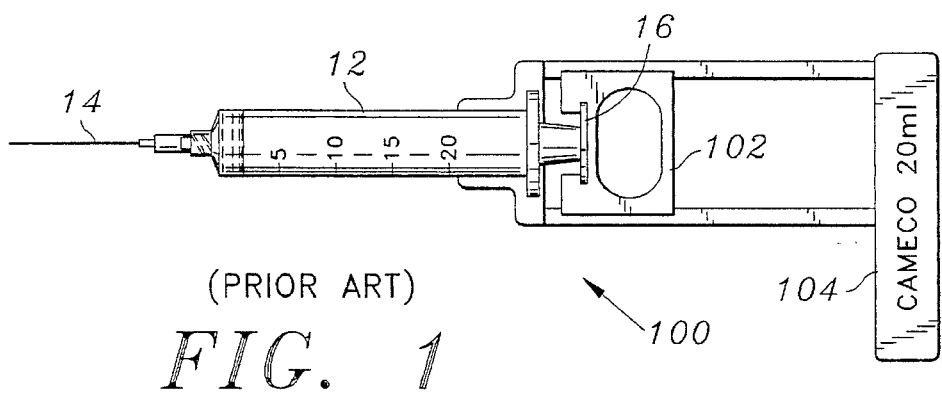
(PRIOR ART)
FIG. 1
(PRIOR ART)
FIG. 2
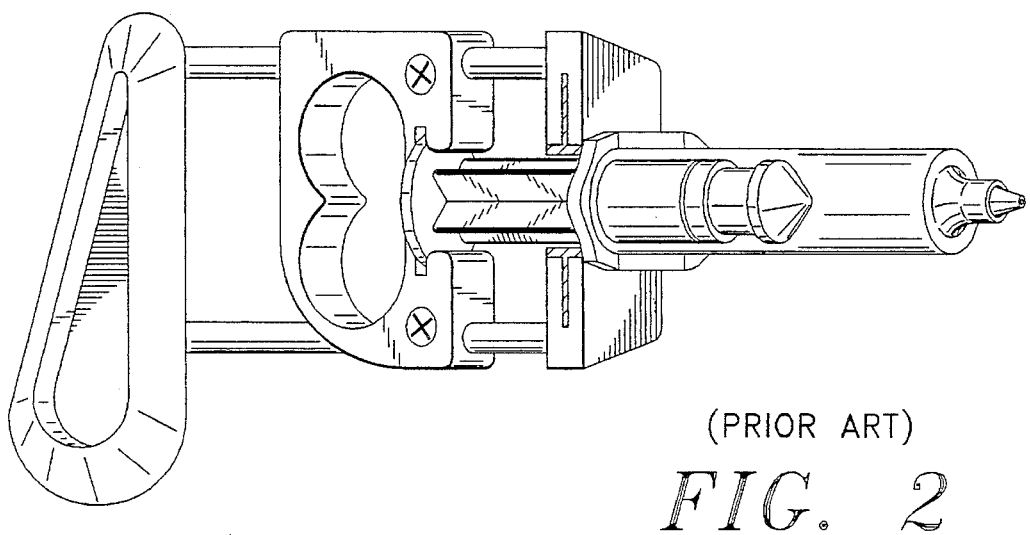
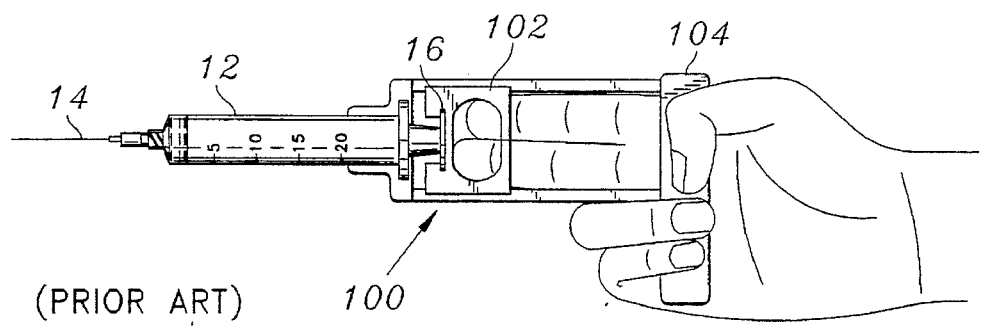
(PRIOR ART)
FIG. 3

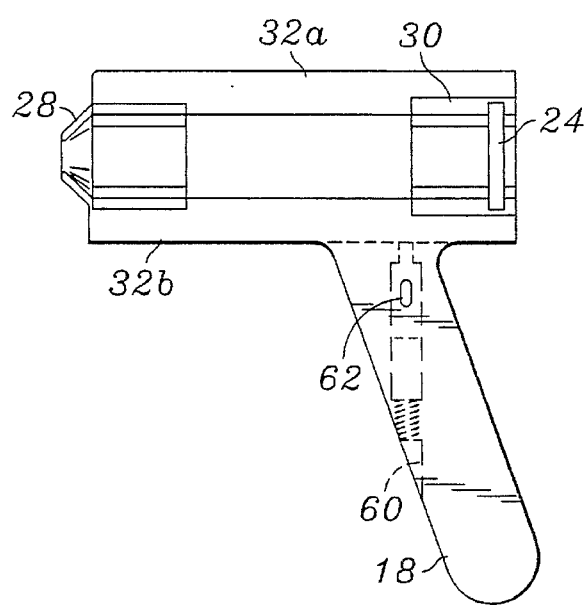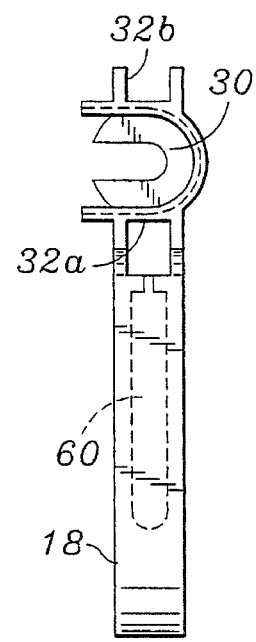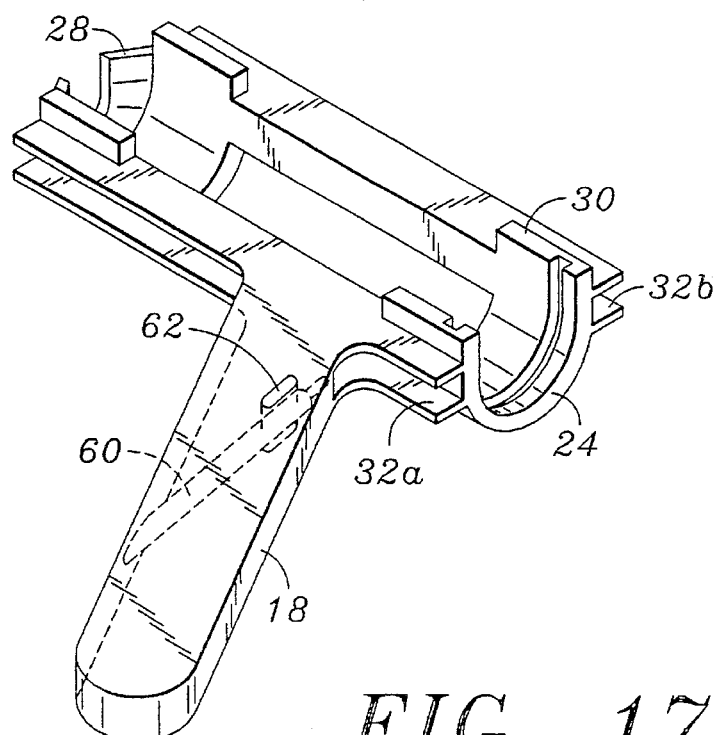
FIG. 15
FIG. 16
FIG. 17

FINE NEEDLE ASPIRATION CYTOLOGY DEVICE SYRINGE HOLDER

RELATED APPLICATIONS

The subject patent application is a continuation-in-part of patent application Ser. No. 08/225,594, filed Apr. 11, 1994, entitled NEEDLE CORE BIOPSY INSTRUMENT, the contents of which are incorporated herein by reference.

FIELD OF THE INVENTION

The present invention relates to tissue extraction devices, and particularly to hand-held devices for extracting tissue samples by fine needle aspiration.

BACKGROUND OF THE INVENTION

Biopsy devices for fine needle aspiration are well known to those skilled in the art. Such devices are useful for obtaining cytologic specimens for examination to confirm the diagnosis of suspected cancers. Generally, such devices are useful in sampling tissue from the breast, the head and neck, lymph nodes, and some gynecologic cancers. Other applications include lung, prostate, and other soft tissue tumor biopsies.

Generally, such biopsy instruments extract samples of tissue through a small needle usually in the range of 25–20 gauge. A vacuum force is usually applied by a standard syringe attached to the needle, while the needle is passed several times in the tissue. A column of cells is then accumulated in the hollow channel of the needle as the needle is passed multiple times into the tumor mass. This procedure can be performed with a syringe alone or in a syringe holding device.

Such syringe holding devices have been in use for at least two decades. A typical device used to perform this technique is disclosed in U.S. Pat. No. 3,819,091, issued to Anders K. Y. Hollander of Boras, Sweden the teachings of which are incorporated herein by reference. Another such device incorporating a syringe holder is disclosed in U.S. Pat. No. 2,472,116, issued to Hyla F. Maynes, the teachings of which are likewise incorporated herein by reference. A still further device which deals with an adjustable aspirating syringe is disclosed in U.S. Pat. No. 2,863,452, issued to Leighten Ogle, and incorporated herein by reference. These devices were primarily issued as syringe holders and were generally not used for fine needle aspiration cytology except for the device designed by Hollander which was specifically designed for aspiration cytology. The device designed by Hollander has a capability of being usable with one hand and further has a capability of utilizing disposable syringes and needle.

The advantages provided by the Hollander device are that it is economical, can be used with one hand, and can provide excellent cytology specimen when used correctly. However, disadvantages also exist with the Hollander device in that the user's hand must be placed behind the piston of the syringe, thereby requiring a distance of approximately 7½ inches to 8½ inches from the user's hand to the tissue to be biopsied. This distance is substantial and makes for difficult needle placement, which can thus lead to an inaccuracy in diagnosis. Additionally, the Hollander device makes no provision for locking the device in a specific position so that a constant amount of suction may be applied. Furthermore, such device produces tension in the hand operating the device which can lead to inaccuracy in obtaining fine needle aspiration specimens.

Accordingly, there exists a substantial need in the art to provide an improved fine needle aspiration cytology device that will place the user's hand closer to the patient (i.e., the tissue to be sampled), and also to provide an aspiration cytology device having means for locking the device in a position to provide a fixed amount of suction. Additionally, there is needed an aspiration device wherein the hand is placed in a natural position of function as well as a device having a stable platform for retaining the syringe. These improvements would be particularly desirable when sampling in confined spaces with compact anatomy, such as tumors of the head and neck where a misplaced needle might lead to a complication.

SUMMARY OF THE INVENTION

The present invention specifically addresses and alleviates the above-mentioned deficiencies associated with the art. More particularly, the present invention comprises an aspiration cytology device comprising a handle and a generally U-shaped slide with trigger in operative combination. The handle is slotted to accommodate a standard syringe and to retain the same in a snug manner during use. The handle is further slotted and channeled to slidably receive the slide, and also includes a channel formed therein for housing a manually operable locking detent mechanism that selectively positions the slide relative the handle. Essentially, the detent locking detent mechanism housed within the handle selectively engages a respective one of a plurality of locking holes formed on the slide. The channel formed in the handle to house the detent locking mechanism is further preferably slotted on both sides for ambidextrous accommodation. In an alternative embodiment, the locking detent mechanism may be removed if that provision is not desired. The slide component comprises a generally U-shaped member defining first and second arms. The arms are designed and configured to slidably engage with the handle such that a respective one of the arms, having the plurality of apertures formed thereon, is oriented toward the locking detent mechanism. The slide also preferably has a trigger attachable thereto. The trigger may be added to the slide mechanism after the slide is passed through and received upon the handle. Once the trigger is so attached, the device is assembled and cannot become separated into its components without removal of the trigger. The slide is further slotted at its rear-most position within the closed end of the generally U-shape for accepting the end of the plunger on the syringe. When the syringe is placed in the appropriate retaining slots formed on the handle and the plunger is retained within the slide, the trigger is maintained at a first, forward-most position and may be easily reached with the index finger of the hand. When the trigger is pulled, it moves the slide to a second, rearward position thereby withdrawing the plunger in the syringe and generating suction through the needle. This pulling action is easily controlled because the hand is advantageously maintained in a natural position of function as the handle on the device is angled.

The device is used by first placing a syringe in the slot formed on the handle and positioning the plunger in the slot formed on the slide. An appropriately sized needle is used, usually in the range of 25–20 gauge, and is placed on the end of the syringe. The plunger of the syringe is initially maintained in the first, forward-most position. The needle is then inserted into the tissue to be sampled. The trigger is then pulled causing the U-shaped slide to retract the plunger such that suction force is created within the barrel of the syringe (i.e., by virtue of the plunger's movement to a rearward position relative to the syringe). The locking detent formed within the handle will automatically be forced into a respective one of a series of holes formed on the bottom of the slide unless the user manually adjusts the detent mechanism, preferably by motioning his thumb to depress a detent knob attachable to the detent and receivable through the handle, to counteract the same. When the desired amount of suction is achieved, the detent knob is released and thus allows the locking detent to lockingly engage a respective hole, thereby allowing the user's index finger and hand to be relaxed. Following this simple to-and-fro motion, the device will accumulate cells in the barrel of the needle. When a sufficient number of passes of the device into the tissue have been made, the locking detent is again deactivated, preferably by depressing the detent knob with the thumb. The plunger of the syringe is therefore allowed to retract further to its closed position which automatically occurs by virtue of the vacuum created in the syringe barrel. The needle is then withdrawn from the tissue. The syringe is removed from the device. The collected cells are then forced onto a slide for cytologic evaluation.

The device is specifically designed to allow the physician user to accurately place a needle into a target area with little or no error by allowing the physician user to place his hand closer to the needle tip as well as place his hand in a position of natural function. The locking detent mechanism of the device is ergonomically designed to be easily manipulated with the thumb of the hand, thus enabling the physician user to keep one hand free at all times. The device is further designed to accommodate a standard syringe and will allow for cost effective and highly efficient tissue sampling.

It is therefore an object of the present invention to provide a fine needle aspiration device that will effectively and efficiently remove cells for cytologic examination.

Another object of the present invention is to provide a fine needle aspiration device that places the hand in a natural position of function so that the manipulation of the device will be precise and simply achieved.

Another object of the present invention is to provide a fine needle aspiration device having means for locking a syringe at a set position such that an amount of suction applied to the tissue is fixed and to further allow the user to relax his hand so that more accurate and precise manipulation can be achieved.

Another object of the present invention is to provide for economic production of the device using heat stable materials such as metal or plastics.

Another object of the present invention is to provide a fine needle aspiration device having a unique design whereby the barrel of the syringe is positioned above the hand, such that the user may place his hand closer to the tip of the needle, and therefore the tissue to be sampled, than current devices.

Another object of the present invention is to provide a fine needle aspiration cytology device which may easily be adapted to CT guided, stereotactic core guided, or ultrasound guided cytology techniques.

Yet another object of the present invention is to provide a fine needle aspiration cytology device that can be easily held and manipulated with one hand, allowing the user to have one hand free.

BRIEF DESCRIPTION OF THE DRAWINGS

FIG. 1 is a side view of a prior art aspiration device, as disclosed in U.S. Pat. No. 3,819,019, with a syringe and needle inserted therein, said device being maintained in a first, closed position;

FIG. 2 is a perspective view of a prior art aspiration device;

FIG. 3 is a side view of the prior art aspiration device disclosed in U.S. Pat. No. 3,819,019 wherein a hand of a user, to manipulate the device, is placed behind the syringe upon the proximal end of the device;

FIG. 15 is a cross-sectional side view of the handle of the fine needle aspiration cytology device;

FIG. 16 is a rear view of the handle of the device;

FIG. 17 is a perspective view of the handle of the device;

DETAILED DESCRIPTION OF THE PREFERRED EMBODIMENT

Figure 4:
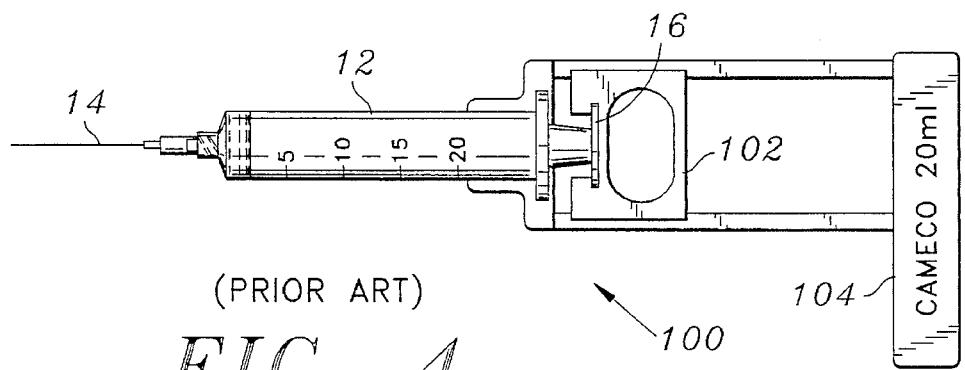
FIG. 4 is a side view of the aspiration device depicted in FIG. 1 being maintained in the first, closed position.

Referring now to FIGS. 6–9 and 11–22, there is shown a fine needle aspiration cytology device 10 according to a preferred embodiment of the present invention. The device 10 is specifically designed and adapted to allow the user of the device 10, typically a physician, to obtain cytologic specimens for examination in a much more accurate and efficient manner than prior art devices, as well as obtain such samples in a manner that minimizes tension in the hands and fingers of the user which continues to be a problem with prior art devices.

FIG. 1 depicts an aspiration device 100 typical of the prior art. The specific device 100 depicted is disclosed in U.S. Pat. No. 3,819,091, issued to Anders K. Y. Hollander, the teachings of which are expressly incorporated herein. The device 100 comprises a hand-held unit capable of releasably engaging a conventional syringe 12 and needle 14. To facilitate handling of the device 100, there is provided a block 102 which orients the fingers of the operating hand toward the piston 16 of the conventional syringe 12, such that the piston 16 may be retracted by pulling upon the block 102. The block 102 is slidably received within a handle 104, the latter having a generally square-like orientation which disadvantageously places the hand in awkward position when the device 100 is utilized to extract tissue.

Figure 5:
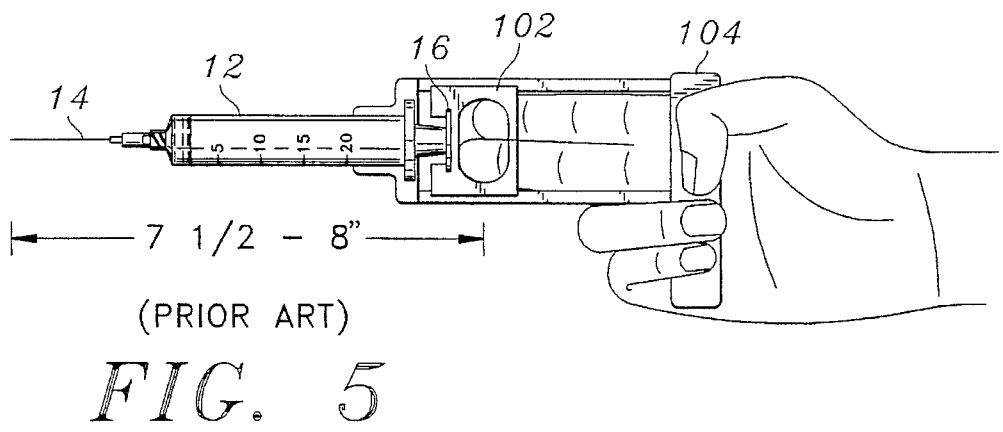
FIG. 5 is a side view of the prior art device depicted in FIG. 4 showing the position of a user's hand and fingers in relation to the device, syringe, and needle tip.

FIG. 3 illustrates how such prior art device 100 is manually grasped while in use. As shown, the orientation of the device 100, due to its generally-squared shape, is recognized in the art as being quite awkward to manipulate. Additionally, FIG. 3 depicts the relative distance between the fingers 106 of the user and the tip of the needle 14a. As those skilled in the art will recognize, this distance, which on the average is approximately 7½ to 8 inches, is considerable and greatly affects the ability of the user to accurately target the area from which biopsies are to be taken. Such prior art device 100 is further depicted in FIG. 4, standing alone, and again in FIG. 5 where there is depicted the approximate distance between the fingers of the user and the tip of the needle 14a.

Figure 6:
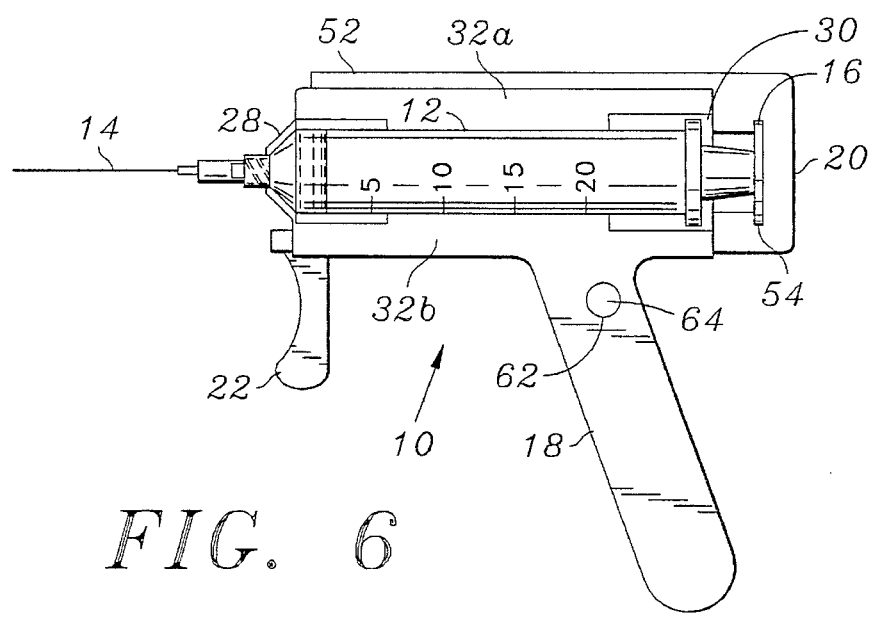
FIG. 6 is a side view of a fine needle aspiration cytology device according to a preferred embodiment of the present invention. The figure further depicts a conventional needle and syringe interconnected thereto.

In contrast to the prior art devices depicted in FIGS. 1–5, there is shown in FIG. 6 an improved fine needle aspiration cytology device 10 according to a preferred embodiment of the present invention. The device 10 is specifically designed and configured to be used in combination with a conventional syringe 12 and needle 14 to obtain cytology specimens, solid tumors, or aspirating cystic lesions. As illustrated, the device 10 is designed to releasably engage and interconnect with the syringe 12 and needle 14 and orient the same in such a manner that biopsies may be collected therein in a much more efficient and accurate manner than prior art devices.

The device 10 is comprised of a handle 18, generally U-shaped slide member 20, and trigger 22 in operative combination, each component being shown alone or in combination in FIGS. 12–22.

Figure 18:
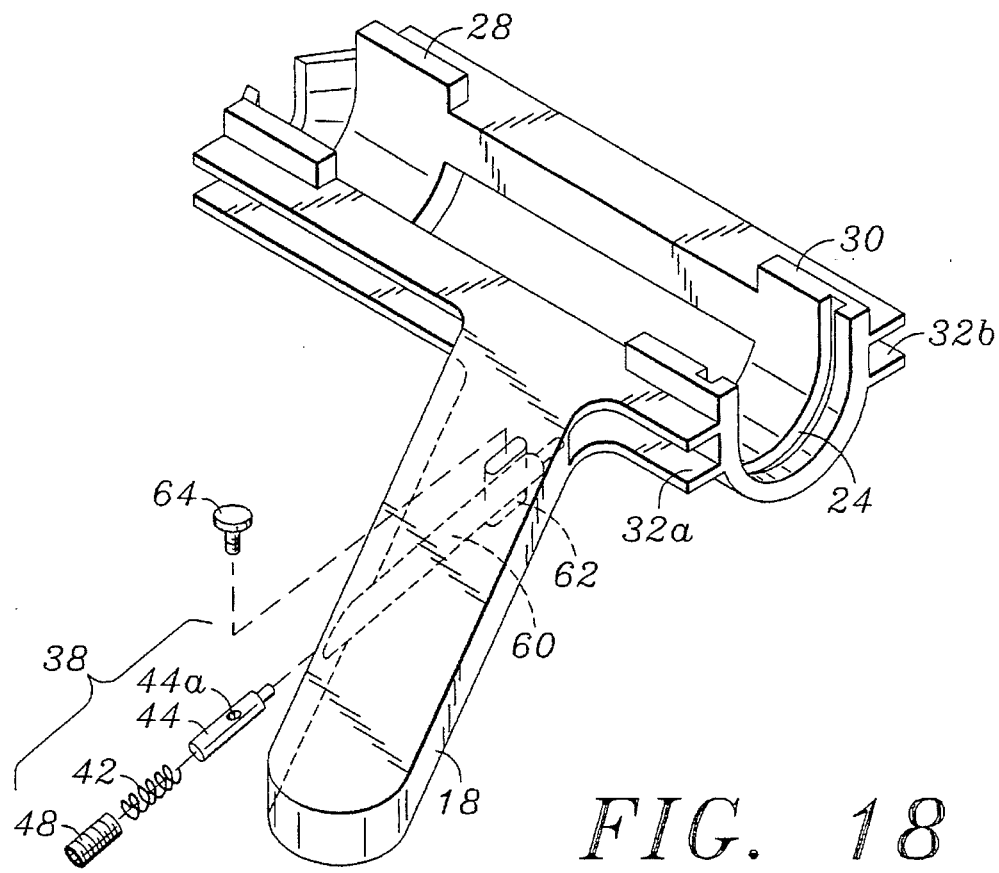
FIG. 18 is an exploded perspective view of the handle and locking detent mechanism of the device.
Figure 19:
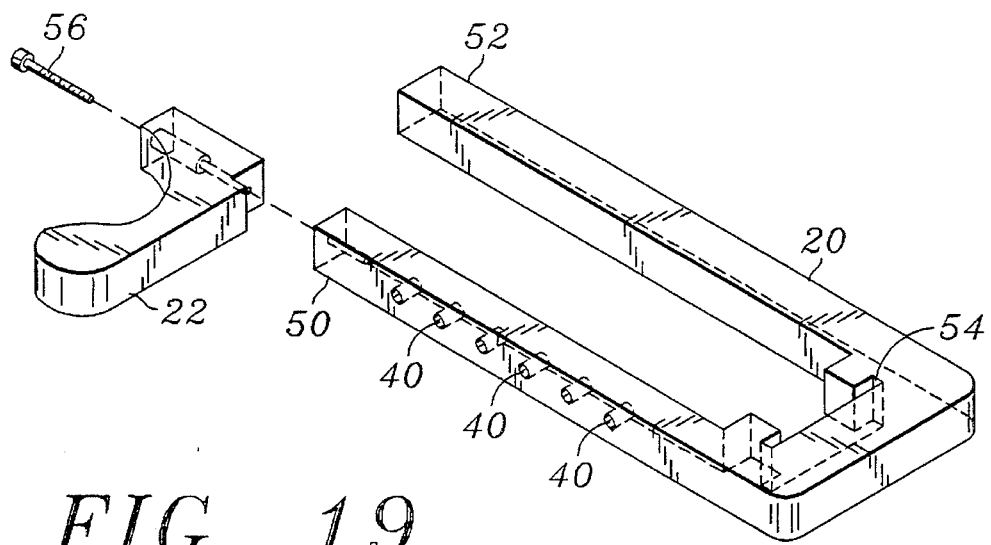
FIG. 19 is an exploded perspective view of the slide and trigger assembly of the device.

With respect to FIGS. 15–18, and more particularly to FIG. 18, there is shown the handle assembly 18 of the device 10. As shown, the handle 18 comprises a front collar 28 formed at the distal end thereof for engaging the front barrel portion of the syringe. The handle further includes a rear collar 30 to accommodate and interconnect with the rear portion of a syringe. There is additionally provided a slot 24 formed within the rear collar to engage with a lip or flange typically formed on syringes so that such conventional syringes may be further secured thereto. Moreover, to provide means for interconnecting with the slide 20, there is formed upon the handle 18 upper and lower grooves or slots 32a, 32b which accommodate the slide assembly 20 so that such assembly 20 may be slidingly received thereonto.

Additionally, the handle component 18 is provided with a locking detent mechanism 38 disposed within the interior thereof, such locking detent mechanism 38 being more clearly depicted in FIGS. 13–18. The detent locking mechanism 38 is housed within channel 60. As will be recognized, the locking detent 44 of the locking detent mechanism 38 extends upwardly through the handle 18 so that the detent 44 may engage a respective one of a plurality of apertures 40 formed on the slide. Such locking detent mechanism 38 advantageously allows the device 10 to be maintained in multiple locking positions, thus alleviating the need for the user to manually maintain the device 10 in fixed positions which, contrary to devices in the prior art, can cause significant fatigue.

The locking detent mechanism 38 disposed within the channel 60, in addition to detent 44, preferably further comprises a spring 42, and detent plug 48. FIG. 18 further illustrates how these components of the locking detent mechanism 38 are received within the channel 60. As shown, the locking detent 44 is axially received within the channel, followed by the spring 42, and then the detent plug 48 which, when screwed within the channel 60, remains resident. Due to the biasing force of the spring 42, the locking detent 44 is axially forced upwardly so as to engage the respective apertures 40 formed on the slide 20. However, to allow for sliding movement of the slide 20, there is provided on the locking detent 44 an aperture 44a into which a knob 64 may be threadably received. Advantageously, knob 64 allows the detent 44 to be forced downwardly against the biasing force of the spring 42, thus permitting the slider 20 to move to and fro upon the handle 18.

To allow the knob 64 to engage with the detent 44 to thus permit the locking detent mechanism 38 to be selectively activated, there is provided a second channel 62 that traverses the channel 60 within which the locking mechanism is received. The second channel 62, which is preferably formed at right angles to the primary channel 60, is formed to have a generally elongate shape to allow the knob 64 to be depressible such that the locking detent 44 may be withdrawn to a point which will not interfere with the sliding movement of the slide 20. In a more preferred embodiment, the second channel 62 traverses the entire width of the handle 18 such that the depressible knob 64 may be connected to the locking detent 44 on either side of the handle 18 to thus allow the device 10 to be used ambidextrously.

Advantageously, such locking detent mechanism 38, by virtue of knob 64 attached thereto, is configured to allow the thumb on the hand of the user operating the device 10 to selectively position the slide 20 relative to the handle 18. As will be appreciated, by depressing the knob 64 of the locking detent mechanism 38, the slide 20 may freely move in forward and rearward directions. Such movement allows the user to draw a vacuum into the syringe 12 connected to the device 10 such that a biopsy sample is drawn into the needle 14. Furthermore, due to the plurality of apertures 40 formed on the bottom side of the slide 20, the device 10 of the present invention advantageously allows the user to selectively position the slide 20 with respect to the handle 18 such that a desired vacuum force can be selectively controlled and further, allows the device 10 to penetrate tissue at various depths while maintained in a locked position.

Figure 12:
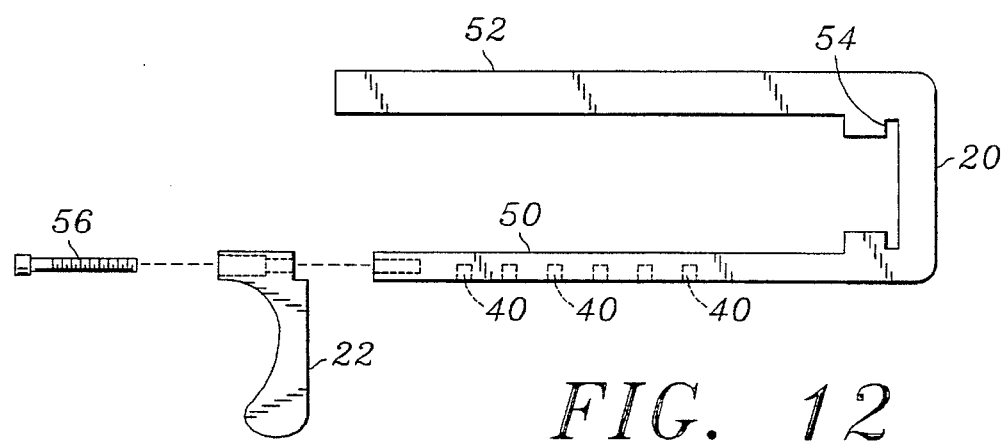
FIG. 12 is a side exploded view of the slide and trigger assembly of the fine needle aspiration cytology device.
Figure 14:
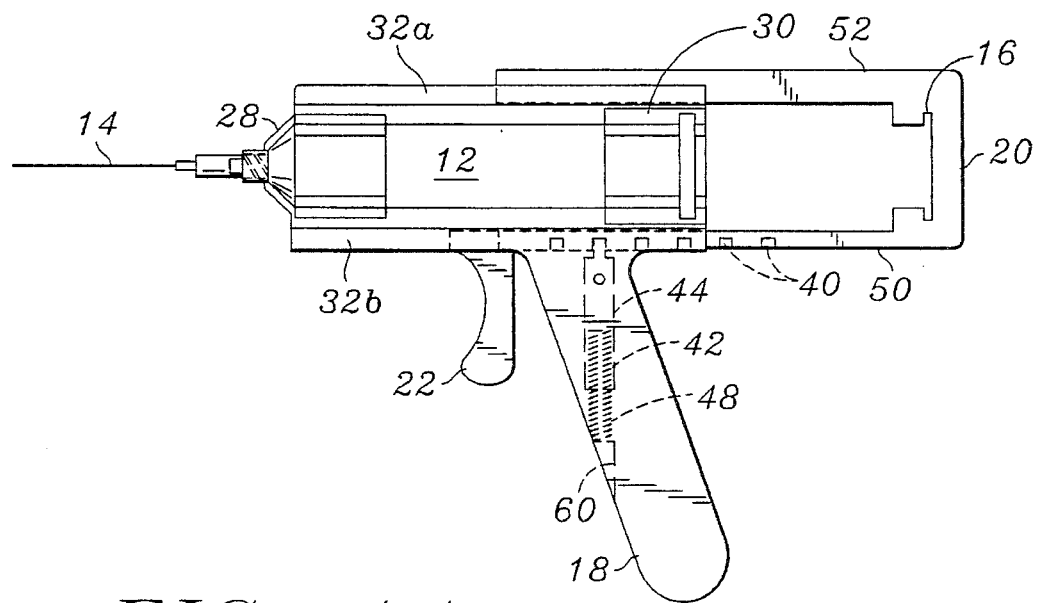
FIG. 14 is cross-sectional side view of the fine needle aspiration cytology device showing the slide in a rearward position relative the handle wherein the locking detent mechanism disposed within the handle is engaged with a respective one of the detent holes formed on the slide.

Referring now to FIGS. 12 and 14, there is illustrated an exploded side view of the slide assembly 20. As illustrated, the slide assembly 20 comprises a generally U-shaped slide member 20 defining first and second arms 50, 52 and further includes a syringe piston slot 54 formed at the closed end thereof. Additionally, the generally U-shaped slide member 20 includes a plurality of apertures 40 formed upon the bottom surface of the first arm 50 thereof for engaging the upwardly extendable locking detent 44, more clearly depicted in FIG. 14. The slide assembly 20 further includes a trigger member 22 attachable to the generally U-shaped slide member 20 preferably by means of screw 56 receivable within a trigger screw hole 56a formed on the distal end of the first arm 50 of the generally U-shaped slide member 20. As those skilled in the art will appreciate, the slide assembly 20 of the present invention, as well as all other parts, are preferably fabricated from durable, sterilizable materials such as metal and/or plastics, such as polycarbonate. Alternatively, the device 10 of the present invention may be fabricated from materials that would enable the device to be disposed of after a single use.

Figure 20:
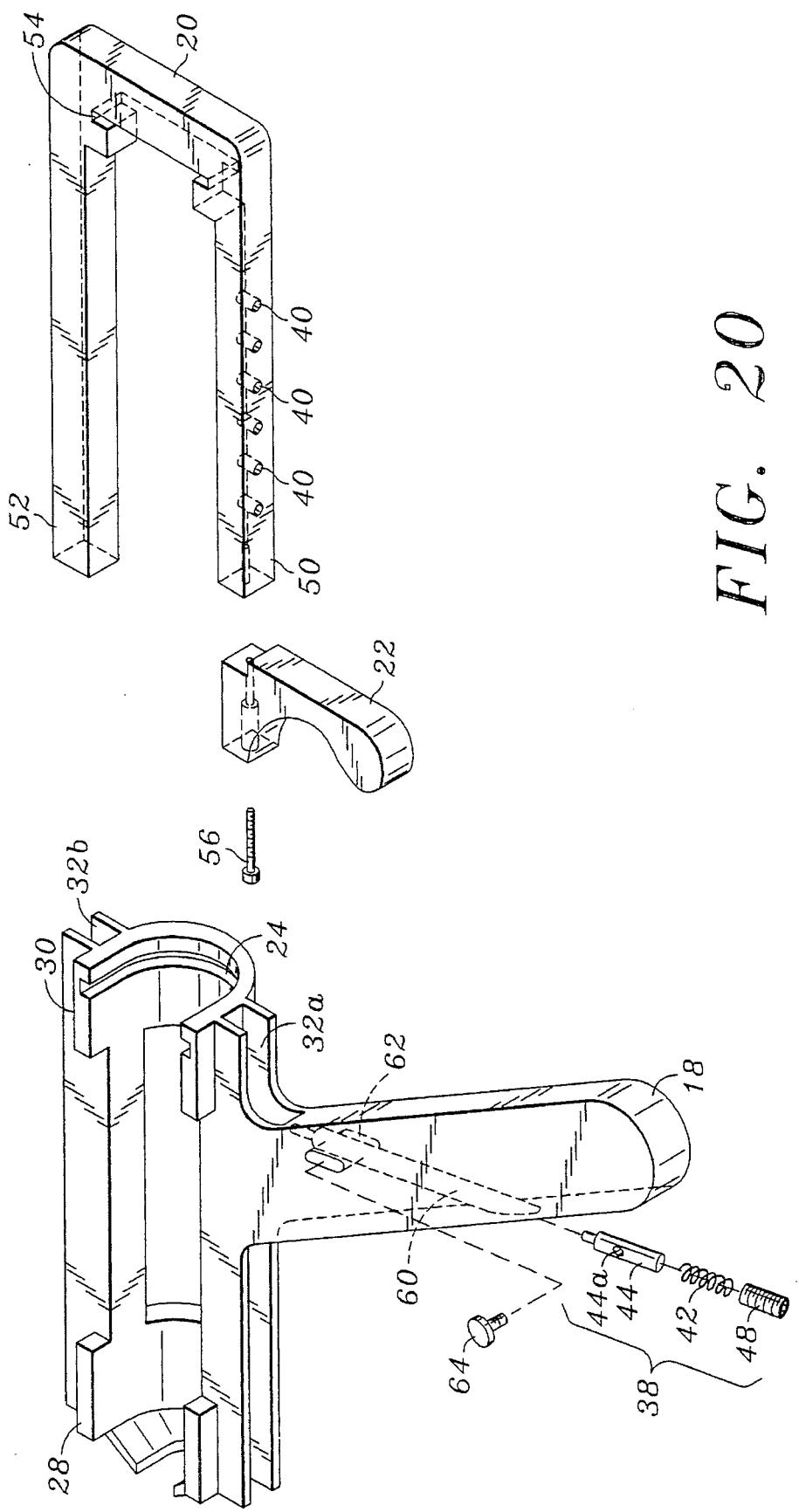
FIG. 20 is an exploded perspective view of the handle assembly, slide, and trigger of the device.

Referring now to FIG. 20, there is shown an exploded view of the components comprising the device 10. The exploded perspective view illustrates how the various components cooperate to form the device 10. Initially, the generally U-shaped slide member 20 is slidably connected to the handle 18 by virtue of arms 50, 52 which are received within grooves 32a, 32b respectively. Once having been slidably engaged thereto, the slide 20 may then have the trigger member 22 screwed thereonto by means of a screw 56, which may be received through the trigger member 22 and into the first or lower arm 50 of the generally U-shaped slide member 20. The knob 64 of the locking detent mechanism 38 may then be depressed and selectively released in the aforementioned manner such that the locking detent 44 may engage a respective one of the plurality of apertures 40 formed on the first or lower arm 50 of the generally U-shaped slide member 20.

Figure 7:
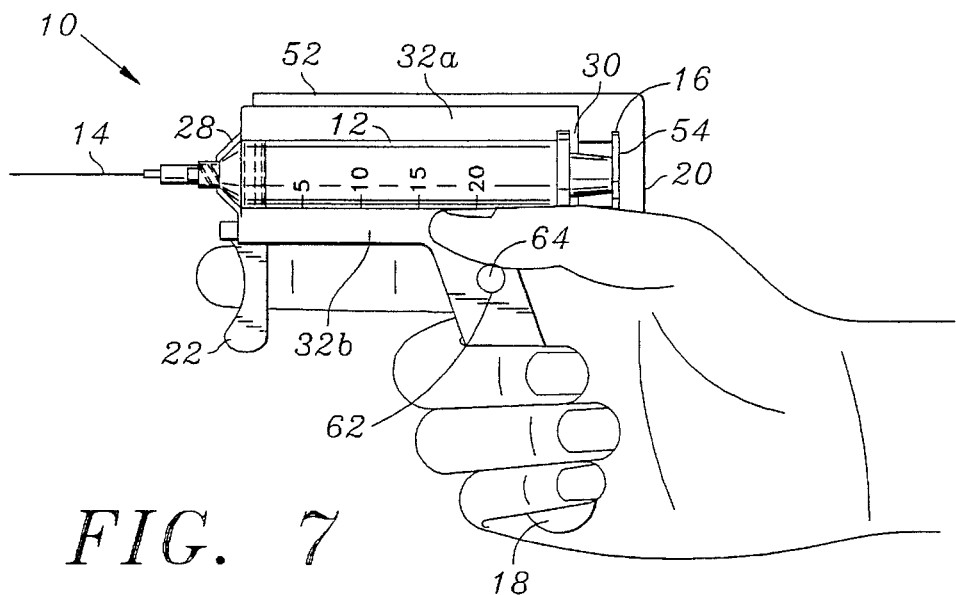
FIG. 7 is a side view of the fine needle aspiration cytology device being held by the right hand of a user.
Figure 8:
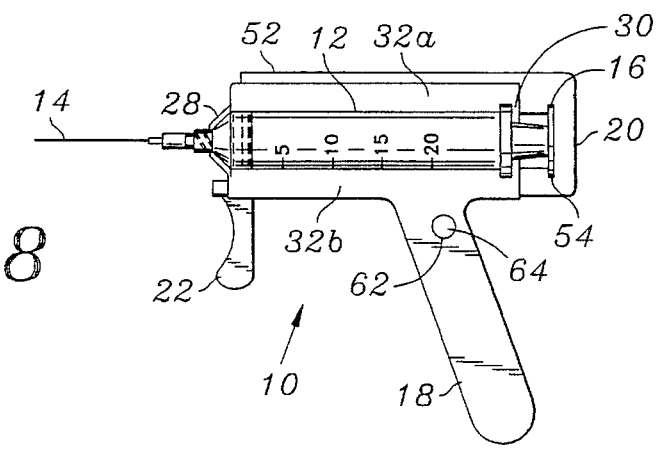
FIG. 8 is a side view of the fine needle aspiration cytology device being maintained in a first position.
Figure 9:
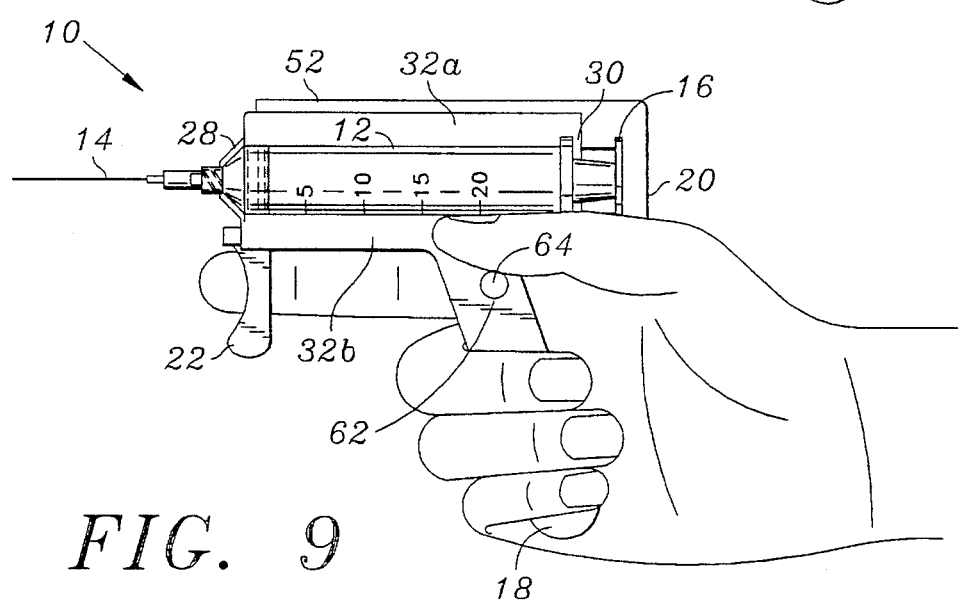
FIG. 9 is a side view of the fine needle aspiration cytology device being maintained in a first position while being held in the right hand of a user.
Figure 13:
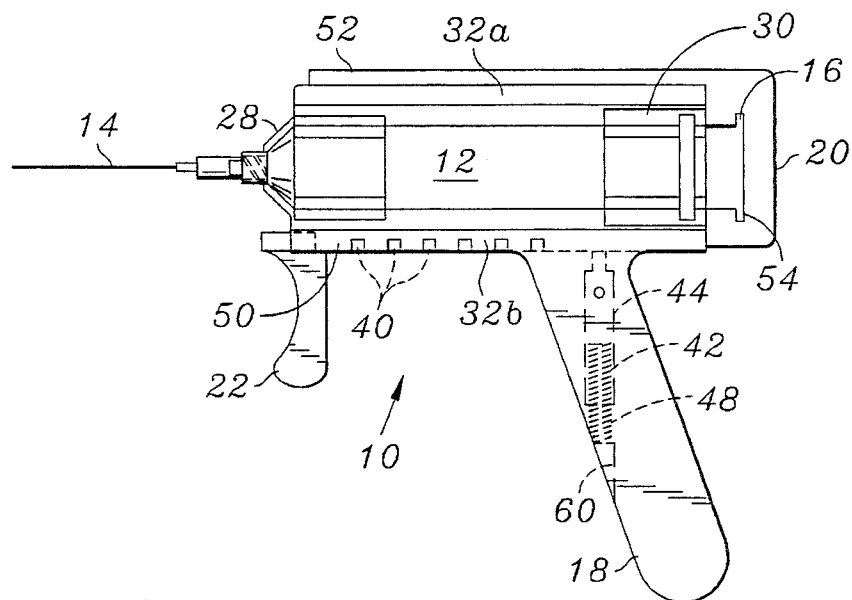
FIG. 13 is a cross-sectional side view of the fine needle aspiration cytology device showing the relative position of the slide with detent holes formed on the bottom arm thereof with respect to a locking detent mechanism disposed within the handle of the device.
Figure 21:
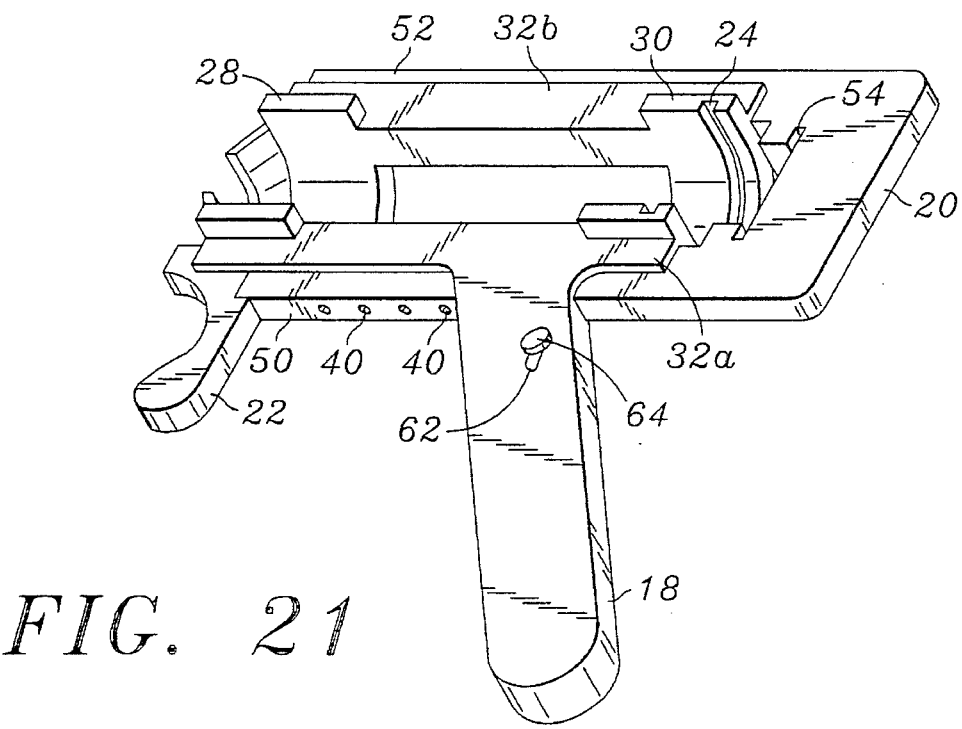
FIG. 21 is a perspective view of the device, as assembled, being maintained in a first forward-most position.

Once having been completely assembled, a generally gun-like structure, as depicted in FIG. 21 is formed. The device 10 may then be interconnected with a conventional syringe, as depicted in FIG. 13. Of particular importance is the fact that the syringe barrel is located above the handle 18 when connected thereto, which thus allows the device 10 to be manipulated such that the hand of the user is maintained in the forward position. FIG. 7 depicts how the hand is maintained in such position when the device 10 is so grasped. Additionally, FIG. 7 depicts the position of the index finger at the trigger 22 which advantageously allows the index finger to be placed at a position far closer to the needle 14, and thus the tissue, than current biopsy devices. In fact, the configuration of the slide 20 in relation to the handle 18 is such that the extended index finger of the operating hand, when holding the device 10, comes to within 1½–2 inches from the position of needle entry. Such closer distance greatly enhances the user's ability to more accurately extract samples from a given tissue mass.

FIG. 21 portrays the device 10 wherein the slide 20 is maintained in a forward-most position. This position would place the piston 16 of the syringe 12 in a forward-most position. Additionally, this position would be suitable for insertion of the needle 14 into the tissue prior to generating any suction within the syringe 12.

Figure 22:
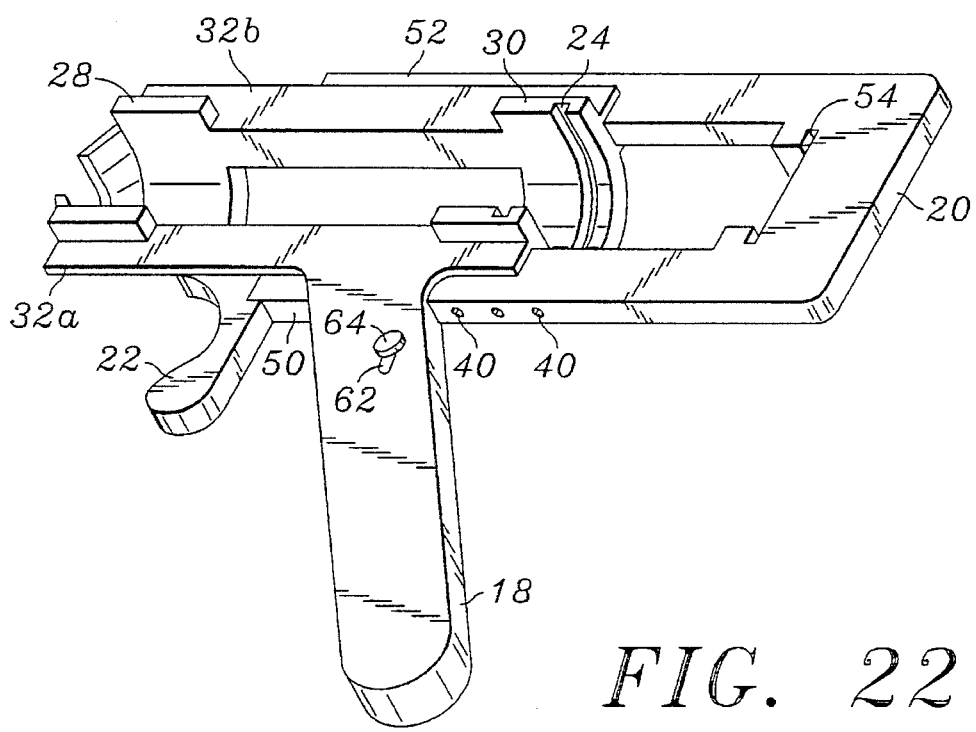
FIG. 22 is a perspective view of the assembled device being maintained in a second, retracted position.

FIG. 22, in contrast to FIG. 21, depicts the device 10 being maintained in a second position wherein the slide 20 is withdrawn to a rearward position, which would, when syringe 12 is placed therein, create a vacuum to be drawn within the syringe 12. Such position would be maintained while a specimen was being extracted from a tissue mass.

Such first and second positions of the device 10, as depicted with the conventional syringe 12 connected therewith, are likewise depicted in FIGS. 13 and 14. FIG. 13 depicts the conventional syringe 12 interconnected with the device 10 such that the plunger 16 of the syringe 12 is received within the notch 54 formed on the base of the generally U-shaped slide member 20. Additionally, the slide 20 is maintained in a forward-most position such that a vacuum force is not generated within the syringe 12 (i.e., the plunger 16 of the syringe 12 is maintained in a forward-most position). FIG. 14, in contrast, depicts the plunger 16 of the conventional syringe 12 being retracted by virtue of the rearward movement of the slide 20 relative the handle 18. Such rearward movement causes a vacuum to generated within the syringe 12 that facilitates the collection of samples from a tissue mass. In order to maintain the position of the slide 20 relative the handle 18, the locking detent mechanism 38 may be activated by manipulating knob 64 in the aforementioned manner. By locking the positioning of the slide 20 relative the handle 18, the user may be able to extract a tissue sample in a manner that is much less fatiguing than conventional prior art devices.

Figure 10:
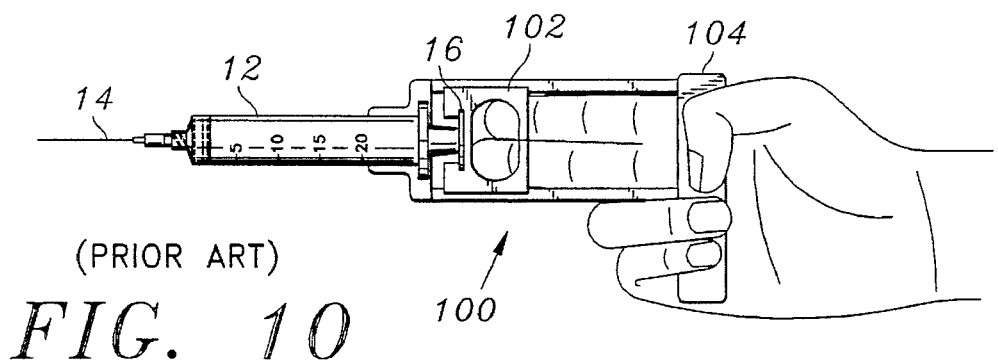
FIG. 10 is a side view of the prior art device depicted in FIG. 1 being held in the right hand of a user.
Figure 11:
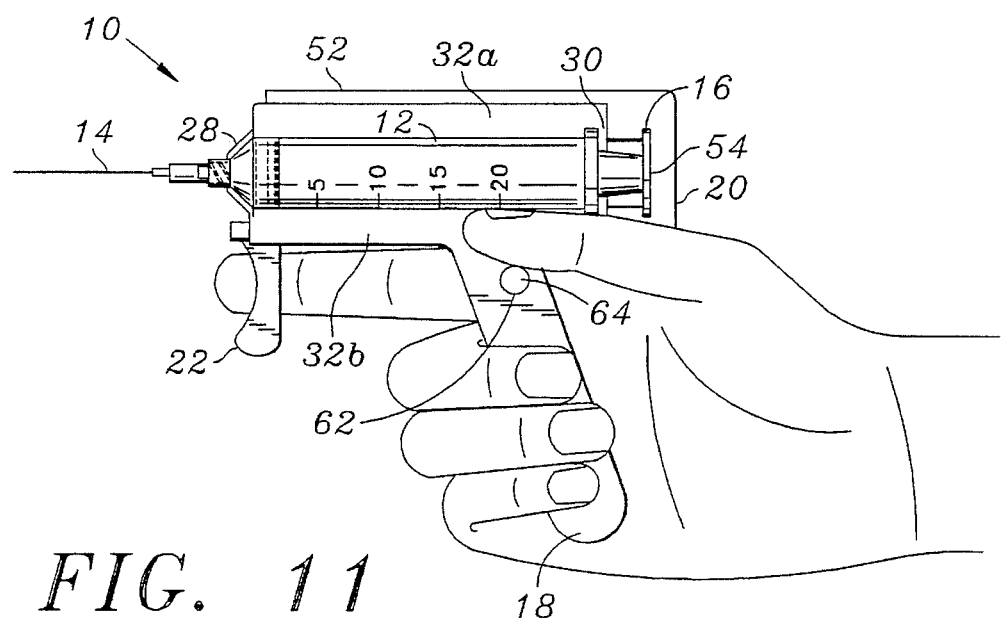
FIG. 11 is a side view of the fine needle aspiration cytology device being held by the right hand of a user.

Further, to illustrate the contrast between the device 10 of the present invention with the prior art device 100 depicted in FIGS. 1–4, there is shown in FIGS. 10 and 11 the relative positioning of the user's hand, with respect to each device 10, 100, when such devices 10, 100 are utilized. As shown in FIG. 10, the prior art device 100 requires the user's hand to be positioned a significant distance away from the needle 14 to be inserted into the patient whereas the device 10 of the present invention, as illustrated in FIG. 11, illustrates how the hand is placed much more closely to the needle 14. Such closer proximity of the user's hand relative the needle 14, which is approximately 1.5 inches to 2 inches, allows the device 10 of the present invention to be more accurate when inserting the needle into the target tissue mass. Additionally, the device 10, due to its ergonomic, generally gun-like structure, allows the user to place his or her hand in a position of natural function as opposed to the rather awkward handle arrangement of the prior art device 100.

There has thus been provided an aspiration cytology device 10 capable of effectively and efficiently obtaining fine needle aspiration specimens. The device 10, by its unique configuration, provides a significant advance in the design of a cytology device. The device 10 specifically obviates the need for the rods and slide block of the previous devices. It facilitates the use of an angled handle and allows forward position of the hand in a heretofore undescribed manner, also not described on previous aspirating devices, is the provision of simplified and easily operated locking detent with variable or staged position. It should be understood that various modifications within the scope of this invention can be made by one of ordinary skill in the art without departing from the spirit thereof. I therefore wish my invention to be defined by the scope of the appended claims as broadly as the art will permit, and in view of the specification if need be.

What is claimed is:

1. A manually operated aspirating device used in combination with a conventional needle and syringe with plunger comprising:

a) a body into which the syringe is received via the side thereof, said body having at least one collar formed thereon for attaching said syringe to said body;

b) a slide slidably attachable to said body, said slide having a slot formed thereon for releasably engaging said plunger, said slide being so attachable to said body such that when said syringe is attached to said body, said slide may selectively position said plunger relative said syringe;

c) a hand grip formed to said body distal of the proximal end of the syringe;

d) said slide comprises a generally U-shaped member having a closed end and a pair of generally parallel arms, said slot for releasably engaging said plunger being formed at the closed end of said generally U-shape;

e) said body includes first and second channels formed therein for slidably engaging a respective one of said pair of arms.

f) a trigger member depending downwardly from a lowermost one of said pair of arms of said generally U-shaped member, said trigger member being so attachable to said generally U-shaped member that when said generally U-shaped member is slidably attached to said body and handgrip, a generally gunlike structure is formed, said trigger providing means for allowing a user to actuate said slide relative said body; and g) wherein during use the hand of the user is placed in a forward position wherein the index finger of a user's hand is oriented toward the target tissue and is positioned from 1 inch to 4 inches proximal the tip of said needle.

2. The device of claim 1 wherein:

a) a respective one of said pair of arms includes a plurality of apertures formed thereon, said apertures being spaced generally about the length of said one of said pair of arms; and b) a detent locking mechanism disposed substantially within said handgrip, said detent locking mechanism having an upwardly spring biased locking detent oriented and configured to selectively engage a respective one of said plurality of apertures, said engagement between said locking detent and said respective one of said plurality of apertures maintaining said slide and said body in releasably rigid attachment.

3. The device of claim 2 wherein said detent locking mechanism further includes a knob protruding outwardly from said handle, said knob allowing the user to selectively engage said locking detent with a respective one of said plurality of apertures, said knob extending outwardly from said handle such that said knob may be manually accessed by the hand of the user.

4. The device of claim 3 wherein said knob of said locking detent mechanism is positioned upon said handgrip so as to be accessed by the thumb of said user.

5. The device of claim 2 wherein when said slide is retracted, a vacuum is generated within said syringe and said needle, said retraction of said slide being selectively controllable by said detent locking mechanism.

6. The device of claim 3 wherein said knob is releasably attachable to said locking detent mechanism on either side of said handle, said attachment to either side of said handle providing means for allowing said device to be used by either the left or right hand of a user.

7. The device of claim 1 wherein said device is fabricated from sterilizable materials.

8. The device of claim 7 wherein said device is fabricated from at least one of the group of materials consisting of:

a) stainless steel;

b) aluminum; and c) heat stable plastic.

9. The device of claim 1 wherein said body includes first and second collars formed thereon for attaching said syringe to said body.

10. A manually operated aspirating device used in combination with a conventional needle and syringe with plunger comprising:

a) a handle releasably attachable to said syringe, said handle comprising at least one collar formed thereon for attaching said syringe to said handle;

b) a slide slidably attachable to said handle, said slide comprising a slot formed thereon for releasably engaging said plunger, said slide being so attachable to said handle that when said syringe is attached to said handle, said slide may selectively position said plunger relative said syringe;

c) said slide comprises a generally U-shaped member having a closed end and a pair of arms, a respective one of said pair of arms includes a plurality of apertures formed thereon, said apertures being spaced about the length of said one of said pair of arms, said slot for releasably engaging said plunger being formed at the closed end of said generally U-shape; and d) said handle comprises first and second channels formed thereon for slidably engaging a respective one of said pair of arms and said handle also comprises a detent locking mechanism disposed therein, said detent locking mechanism comprising an upwardly spring biased locking detent oriented and configured to selectively engage a respective one of said plurality of apertures, said engagement between said locking detent and said respective one of said plurality of apertures maintaining said slide and said handle in releasably rigid attachment.

11. The device of claim 10 wherein said detent locking mechanism further comprises a knob protruding outwardly from said handle, said knob allowing the user to selectively engage said locking detent with a respective one of said plurality of apertures, said knob extending outwardly from said handle such that said knob may be manually accessed by the hand of the user.

12. The device of claim 11 wherein said knob of said locking detent mechanism is positioned upon said handle so as to be accessed by the thumb of said user.

13. The device of claim 10 wherein when said slide is retracted, a vacuum is generated within said syringe and said needle, said retraction of said slide being selectively controllable by said detent locking mechanism.

14. The device of claim 11 wherein said knob is releasably attachable to said locking detent mechanism on either side of said handle, said attachment to either side of said handle providing means for allowing said device to be used by either the left or right hand of a user.

15. The device of claim 10 wherein said device is fabricated from sterilizable materials.

16. The device of claim 10 wherein said device is fabricated from at least one of the group of materials consisting of:

a) stainless steel;

b) aluminum; and c) heat stable plastic.

17. The device of claim 10 wherein said handle comprises first and second collars formed thereon for attaching said syringe to said handle.

* * * * *